United States Patent
Allred et al.

(10) Patent No.: US 9,883,989 B2
(45) Date of Patent: Feb. 6, 2018

(54) STABLE DENTAL VARNISH COMPOSITIONS AND METHODS OF MANUFACTURE AND USE

(71) Applicant: ULTRADENT PRODUCTS, INC., South Jordan, UT (US)

(72) Inventors: Peter M. Allred, Bluffdale, UT (US); Christian D. Kasteler, Murray, UT (US)

(73) Assignee: Ultradent, Products, Inc., South Jordan, UT (US)

(*) Notice: Subject to any disclaimer, the term of this patent is extended or adjusted under 35 U.S.C. 154(b) by 0 days.

(21) Appl. No.: 14/775,470

(22) PCT Filed: Mar. 13, 2014

(86) PCT No.: PCT/US2014/025323
§ 371 (c)(1),
(2) Date: Sep. 11, 2015

(87) PCT Pub. No.: WO2014/151269
PCT Pub. Date: Sep. 25, 2014

(65) Prior Publication Data
US 2016/0022548 A1    Jan. 28, 2016

Related U.S. Application Data

(60) Provisional application No. 61/794,767, filed on Mar. 15, 2013.

(51) Int. Cl.
| | |
|---|---|
| *A61K 8/97* | (2017.01) |
| *A61Q 11/00* | (2006.01) |
| *A61K 8/365* | (2006.01) |
| *A61K 8/21* | (2006.01) |
| *A61K 6/02* | (2006.01) |
| *A61K 6/027* | (2006.01) |
| *A61K 6/00* | (2006.01) |
| *A61K 8/24* | (2006.01) |
| *A61K 8/92* | (2006.01) |
| *A61K 8/19* | (2006.01) |
| *A61C 19/06* | (2006.01) |

(52) U.S. Cl.
CPC .......... *A61K 6/0017* (2013.01); *A61C 19/063* (2013.01); *A61K 8/19* (2013.01); *A61K 8/21* (2013.01); *A61K 8/24* (2013.01); *A61K 8/365* (2013.01); *A61K 8/922* (2013.01); *A61K 8/97* (2013.01); *A61Q 11/00* (2013.01); *A61K 2800/262* (2013.01)

(58) Field of Classification Search
USPC ................. 424/49, 52; 433/215, 216, 217.1; 514/782
See application file for complete search history.

(56) References Cited

U.S. PATENT DOCUMENTS

| | | | |
|---|---|---|---|
| 3,817,768 A | 6/1974 | Aldrich | |
| 6,361,761 B1 | 3/2002 | Joziak et al. | |
| 6,497,858 B1* | 12/2002 | Takatsuka | A61K 6/083 424/49 |
| 2008/0092776 A1 | 4/2008 | Stockl et al. | |
| 2008/0119588 A1 | 5/2008 | Orlwoski et al. | |
| 2009/0142282 A1 | 6/2009 | Kendall et al. | |
| 2009/0191279 A1 | 7/2009 | Kennard et al. | |
| 2010/0247456 A1* | 9/2010 | Niederman | A61K 8/69 424/52 |

FOREIGN PATENT DOCUMENTS

| | | |
|---|---|---|
| CN | 1511027 | 7/2004 |
| DE | 10138242 A1 | 2/2003 |
| EP | 1400240 A1 | 3/2004 |
| JP | H1095726 A | 4/1998 |

OTHER PUBLICATIONS

Kumler, et al., "The Acid Strength of Mono and Diesters of Phosphoric Acid. The n-Alkyl Esters from Methyl to Butyl, the Esters of Biological Importance, and the Natural Guanidine Phosphoric Acids", Jan. 1943, 8 pages. Available at <<http://pubs.acs.org/doi/pdf/10.1021/ja01252a028>>.
Chinese Office Action issued in Chinese Application No. 201480026829.7 dated Feb. 24, 2017.

* cited by examiner

*Primary Examiner* — Lezah Roberts
(74) *Attorney, Agent, or Firm* — Workman Nydegger (57) ABSTRACT

Fluoride varnish compositions for temporary application and adhesion to a person's teeth include a carrier that remains stable and translucent during storage. The compositions include a carrier comprising a stable and translucent resin and a fluoride ion source (e.g., a fluoride salt such as sodium fluoride) dispersed within the carrier so as to provide biologically available fluoride ions to teeth being treated. The carrier resists formation of solids that can plug a 25 gauge or smaller syringe brush applicator tip. The compositions may also include an adhesion promoting agent comprising an alkyl phosphoric acid. The composition adheres only temporarily to tooth tissue (e.g., for a period of at least about 4 minutes, but not more than about 1 year), after which the composition spontaneously wears away as a natural result of the action of the tongue, saliva and/or other factors.

21 Claims, 4 Drawing Sheets

STABLE DENTAL VARNISH COMPOSITIONS AND METHODS OF MANUFACTURE AND USE

BACKGROUND OF THE INVENTION

1. The Field of the Invention

The present invention generally relates to dental treatment compositions, including fluoride treatment compositions.

2. The Relevant Technology

In the field of dentistry, fluoride compositions are applied to a patient's teeth as part of a routine dental cleaning Application of fluoride has been widely recognized as a method for preventing tooth decay. According to one method, a fluoride gel composition is dispensed within a dental tray, after which the tray is placed over the patient's teeth. The tray holds the fluoride gel composition adjacent to the patient's teeth, and after a desired amount of time (e.g., a minute or less), the tray is removed and the remaining gel composition is rinsed off the patient's teeth.

Alternatively, fluoride varnish compositions can be applied to a person's teeth and left in place for days or weeks. In many cases fluoride varnish compositions are yellow or opaque white and therefore are not aesthetically pleasing. In addition, fluoride varnish are typically dispensed from a container using a brush. The practitioner typically dips the brush into the container and then paints the fluoride varnish onto the patient's teeth like fingernail polish. This dipping and painting procedure is repeated several times, perhaps once for each tooth, which made the procedure cumbersome and potentially messy.

And while it may be desirable to dispense a fluoride varnish composition from a syringe and onto a patient's teeth using a brush tip, existing fluoride compositions have lacked sufficient stability and shelf life to remain as a stable gel over time during storage and prior to use. As a result, they can become gritty over time, which causes plugging of the brush tip, especially narrow gauge tips that are suitable for dispensing relatively low viscosity fluids such as fluoride varnish compositions. Formation of solids also reduces initial translucency and causes fluoride varnish compositions to become hazy or white over time, reducing their aesthetic appeal.

SUMMARY OF THE PREFERRED EMBODIMENTS

Disclosed herein are stable dental varnish compositions for application to a person's teeth, which comprise a stable liquid or gel carrier and an active agent dispersed within the carrier. The carrier includes a solvent, a resin component and an acidifying component. The resin component comprises an acidic hydrogenated wood rosin that has been at least partially neutralized to raise its pH to above 5. The acidifying component comprises at least organic or inorganic acid that lowers the pH of the liquid or gel carrier to below 5.

The dental varnish compositions can be formulated to be stable for at least about 3 months so as to remain translucent and not form solids that plug a 25 gauge or smaller syringe brush applicator tip. According to one embodiment, the dental varnish composition can be stable for at least about 6 months so as to remain translucent and not form solids that plug a 30 gauge or smaller syringe brush applicator tip.

According to one embodiment, the dental varnish composition may further comprise an organo phosphoric acid having at least one alkyl group. The organo phosphoric acid can be useful to increase adhesion of the varnish composition to a tooth surface.

According to one embodiment, the active agent comprises a fluoride ion source so that the dental varnish composition is a fluoride varnish. Alternatively or in addition to fluoride ions, the active agent may include at least one of a calcium ion source or a phosphate ion source. If the fluoride varnish composition is anhydrous, premature reaction and precipitation of fluoride and calcium ions is minimized or prevented.

A method of manufacturing a stable dental varnish composition for application to a person's teeth comprises: (1) preparing a stable liquid or gel carrier by mixing together an acidic hydrogenated wood rosin that has been at least partially neutralized to raise its pH to above 5, a solvent, and an acidifying agent to lower the pH of the carrier to below 5; and (2) adding an active agent before, during or after formation of the stable liquid or gel carrier.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings, in which.

DETAILED DESCRIPTION OF THE PREFERRED EMBODIMENTS

I. Introduction

Disclosed herein are stable dental varnish compositions for use in providing a desired treatment to a person's teeth. The stable dental varnish compositions include a liquid or gel carrier that is formulated so that the dental varnish composition remains stable and translucent over time (e.g., for at least about 3 months) and does not form solids that plug a 25 gauge or smaller syringe brush applicator tip. Surprisingly, increased stability is provided by formulating the liquid or gel carrier to include an acidic hydrogenated wood rosin that has been at least partially neutralized with a base to raise its pH to above 5 (e.g., to about 6-7) and then acidifying the carrier to below 5 (e.g., to about 4 or less).

Dental varnish compositions prepared in this manner have substantially greater stability over time compared to varnish compositions made using an acidic hydrogenated wood rosin that has not been neutralized. Such increased stability is achieved even when acidification of the neutralized hydrogenated wood rosin causes the composition to have the same pH as a composition made using acidic hydrogenated wood rosin that is not neutralized with a base.

II. Exemplary Dental Varnish Compositions

Exemplary dental varnish compositions as disclosed herein include a stable liquid or gel carrier and an active agent dispersed within the carrier. a stable liquid or gel carrier and an active agent dispersed within the carrier. The carrier typically comprises a solvent, a resin component and an acidifying component. The resin component advantageously includes an acidic hydrogenated wood rosin that has been at least partially neutralized to raise its pH to above 5. The acidifying component may include at least organic or inorganic acid included in an amount in order to lower the pH of the liquid or gel carrier to below 5.

An example of a suitable resin component is Foral® NC synthetic resin, which is manufactured by Pinova, Inc., Bruswick, Ga., USA, and is the partial sodium resinate of the highly hydrogenated wood rosin, Foral® AX resin, also manufactured by Pinova, Inc. Foral® AX is a thermoplastic, acidic resin produced by hydrogenating wood rosin to a high degree. According to Product Data Sheet, Foral® AX Synthetic Resin, provided by Pinova, Inc., http://www.pinova-solutions.com/docs/Foral%20AX.pdf, Foral® AX is the "most highly stabilized rosin commercially available". Compared to a competitor's resin, Foral® AX "has better initial color and color retention, and even greater resistance to oxidation". Id. Foral Foral® AX acidic hydrogenated wood rosin has a softening point (Ring & Ball, minimum) of 66° C., a color (USRG rosin scale, maximum) of XB, an acid number (minimum) of 158 mg KOH/g, an abietic acid (UV, maximum) value of 0.2%, and refractive index at 100° C. (maximum) of 1.4970. Id.

By way of comparison, Foral® NC is similar to Foral® AX except that an "added benefit of the partial sodium neutralization is an increase in softening point and glass transition temperatures, which allows Foral NC to be packaged as free-flowing pastilles in easily handled bags." Product Data Sheet, Foral® NC Synthetic Resin, provided by Pinova, Inc., http://www.pinovasolutions.com/docs/Foral%20NC.pdf. Foral Foral® NC sodium resinate of the highly hydrogenated wood rosin Foral AX has a softening point (Ring & Ball) of 78-92° C. (typically 83° C.), a color (USRG, maximum) of X (typically XB), an acid number of 120-138 mg KOH/g (typically 126 mg KOH/g), and a typical abietic acid value of <2%. Id.

When formulating dental varnish compositions using Foral® AX as the sole hydrogenated rosin, the resulting varnish has a pH of about 3. Such varnish compositions are initially highly translucent and have good flow properties, which permits them to be dispensed through a narrow gauge syringe brush tip onto a person's tooth surfaces. However, after a few months (e.g., 3 months), such dental varnish compositions can form precipitates, which can cause them to become gritty and less translucent, causing loss of aesthetic appeal and, worse, plugging of the syringe brush applicator tip. By comparison, substituting at least a portion of the Foral® AX with Foral® NC, which is less acidic and has a higher pH, and then adding an acid to lower the pH so that the varnish composition has the same or similar pH as varnishes made using Foral® AX as the sole hydrogenated rosin results in a varnish composition that is substantially more stable over time. Substituting at least a portion of Foral® AX with Foral® NC and then acidifying the composition to have same low pH unexpectedly reduces or eliminates formation of precipitates that reduce translucency and cause syringe tip plugging. This result is surprising and unexpected and would not be predicted based on a comparison of the Product Data Sheets of these products provided by Pinova, Inc.

Example acids that can be used to lower the pH of the liquid or gel carrier containing a base neutralized acidic hydrogenated wood rosin include organic acids and inorganic acids, such as citric acid, phosphoric acid, boric acid, malic acid, and the like. The acid can be added in order to adjust the pH of the liquid or gel carrier containing a base neutralized acidic hydrogenated wood rosin to less than 5, preferably less than about 4.5, more preferably less than about 4, and most preferably to less than about 3.5. According to one embodiment, the pH can be lowered to about 3 or below.

The dental varnish compositions can be formulated to be stable for at least about 3 months so as to remain translucent and not form solids that plug a 25 gauge or smaller syringe brush applicator tip. According to one embodiment, the dental varnish composition can be stable for at least about 6 months so as to remain translucent and not form solids that plug a 30 gauge or smaller syringe brush applicator tip.

In addition to the main resin component, which is the aforementioned acidic hydrogenated wood rosin that has been at least partially neutralized to raise its pH to above 5, the dental varnish composition may optionally include one or more auxiliary resins. Examples of auxiliary resins include natural resins, non-hydrogenated wood rosins, acidic hydrogenated wood rosins, synthetic resins, colophonium, shellac, and combinations thereof. The auxiliary resins are typically hydrophobic, substantially insoluble in water, and freely soluble in alcohol, benzene, ether, glacial acetic acid, oils, and carbon disulfide. Various materials that are individually referred to as "colophonium" include Canadian balsam, Olibanum balsam, Elemi resin, Opopanax resin, Tolu balsam, Peruvian balsam, and Poly-Pale™ resin, which is a partially dimerized rosin available from Eastman Chemical, located in Kingsport, Tenn. Examples of hydrogenated wood rosins include the aforementioned Foral® AX, a fully hydrogenated tree rosin, Staybelite® resin, a partially hydrogenated wood rosin, and Endere® S, a highly hydrogenated allergen tested resin from wood rosin feedstock. Other rosins or rosin derivatives include Pexite® FF, an acidic resin extracted from pine tree stumps, Pexalyn® 295, a synthetic, acid functionalized resin from wood rosin feedstock, Pentalyn® FC, a pentaerythritol ester of maleic anhydride-modified wood rosin, Staybelite® Ester 10-A, an ester of hydrogenated rosin, Hercolyn® D, a methyl ester of hydrogenated wood rosin, Pentalyn® H-A, a pentaerythritol ester of hydrogenated rosin.

The one or more resin components may be included in the dental varnish compositions in various amounts, such as in an amount in a range of about 20% to about 90% by weight, preferably in a range of about 25% to about 80% by weight, more preferably in a range of about 35% to about 75% by weight, and most preferably in a range of about 40% to about 70% by weight.

Dental varnish compositions as disclosed herein may include any desired active agent. For example, the active agent can be a fluoride ion source that provides fluoride treatment to a person's tooth. Instead of or in addition to the fluoride ion source, the active agent may comprise a calcium ion source and/or a phosphate ion source. Even though calcium ions and fluoride ions can react in water to form an insoluble calcium fluoride precipitate, providing a dental varnish composition that is anhydrous (e.g., so as to have a water content of less than 2%, preferably less than about 1.5%, more preferably less than about 1%, and most preferably less than about 0.5%) prevents premature reaction and precipitation. Once applied to a person's teeth, such reaction can beneficially occur on or in the teeth in the presence of saliva.

Examples of fluoride ion sources include sodium fluoride, $BiF_3$, $SnF_2$, $ZnF_2$, KF, $CaF_2$, $ZrF_4$, sodium mono-fluoro-phosphate ($Na_2FPO_3$), hexafluorosilicic acid, sodium hexafluorosilicate, or combinations thereof. When included, the fluoride ion source (e.g., sodium fluoride) may be included in an amount in a range of about 0.1% to about 10% by weight, preferably in a range of about 1% to about 8% by weight, and more preferably in a range of about 2.5% to about 7% by weight.

Examples of calcium and phosphate ion sources include calcium phosphate, calcium nitrate, calcium glycerophosphate, calcium gluconate, calcium chloride, sodium phosphates, sodium polyphosphates, sodium pyrophosphates, and potassium phosphates. Calcium and phosphate ion sources, when included, can be in a range of about 0.1-5% by weight of the varnish composition.

According to one embodiment, the dental varnish composition may further include an organo phosphoric acid (or phosphoric acid ester) that can enhance adhesion of the dental varnish composition to tooth surfaces. The organo phosphoric acid can comprise an alkyl phosphoric acid (also referred to as an alkyl phosphoric acid ester) having from 3 to about 30 carbon atoms in the alkyl group. Mono-alkyl phosphoric acid esters are particularly useful, although di-alkyl phosphoric acid components may alternatively and/or additionally be used. The generic chemical structure of an exemplary organo phosphoric acid is as follows:

"R" represents an alkyl group, which may have from 3 to about 30 carbon atoms. More preferably the alkyl group may include from about 5 to about 30 carbon atoms, more preferably from about 10 to about 25 carbon atoms, and most preferably from about 15 to about 22 carbon atoms. Hexadecyl phosphoric acid (also referred to as hexadecane phosphate) (having 16 carbon atoms) and docosyl phosphoric acid (having 22 carbon atoms) have been found to provide excellent adhesion properties to the carrier. Docosyl phosphoric acid is also believed to exhibit anti-microbial (specifically anti-viral) properties. Structures for both hexadecyl phosphoric acid and docosyl phosphoric acid, respectively, are shown below:

According to one embodiment, the alkyl groups can be fully saturated so that they contain no polymerizable groups as the compositions are intended to adhere relatively weakly to the tissue, not form a permanent bond with underlying tooth tissue. It is believed that the hydrophilic phosphoric acid groups have an affinity (e.g., through hydrogen bonding and/or ionic forces) to hydrophilic tooth surfaces, which contain high quantities of minerals (e.g., calcium-based minerals).

Although adhesion promoting agents having alkyl groups with from 3 to about 30 carbon atoms have been found to be useful, it may be possible to employ an adhesion promoting agent having at least one alkyl group that includes significantly more carbon atoms. For example, it may be possible to use alkyl groups up to one thousand, ten thousand, or even 100,000 or more by diluting the adhesion promoting agent with appropriate solvents.

When included, the organo phosphoric acid component may be included in any desired amount, for example in a range of about 0.5% to about 40% by weight, preferably in a range of about 1% to about 30% by weight, more preferably in a range of about 3% to about 20% by weight, and most preferably in a range of about 5% to about 15% by weight. The use of higher molecular weight, longer alkyl chain adhesion promoting agents may require relatively lower concentrations, which may even be less than 0.5% depending on the degree of dilution (e.g., with a solvent) required to form a composition having the desired consistency.

The liquid or gel carrier will typically include one or more solvents into which the resin materials are dissolved to provide a varnish composition having a desired consistency and flow properties. Ethanol is a useful solvent as it is non-toxic and generally safe for use in the oral cavity, although other solvents (e.g., acetone or isopropyl alcohol) could alternatively be used. If included, the solvent is typically selected so that it evaporates relatively quickly after the composition is applied to the teeth in order for the dental varnish composition to form a film of solid varnish material on the tooth surface. The one or more solvents are typically included in an amount in a range of 5% to about 75% by weight, preferably in a range of about 10% to about 60% by weight of the composition, more preferably in a range of about 15% to about 50% by weight, and most preferably in a range of about 20% to about 45% by weight.

One or more solubilizing agents, such as one or more polyoxyethylene emulsifiers (e.g., polysorbates), may advantageously be included to help prevent phase separation of the various carrier components. Exemplary solubilizing agents include various polysorbates (e.g., polysorbate 20, polysorbate 40, polysorbate 60, polysorbate 80), although other emulsifiers may also be used. Polysorbate 80 (e.g., Tween® 80), which includes a monooleate type fatty acid associated with the polyoxyethylene sorbitan part of the molecule, is a particularly useful solubilizing agent. The one or more solubilizing agents may be included in an amount in a range of about 0.001% to about 3% by weight, preferably in a range of about 0.01% to about 1% by weight, and more preferably in a range of about 0.1% to about 0.5% by weight.

Examples of flavorants that may be included are bubble gum, peach, tropical punch, grape, watermelon, lemon-lime, cinnamon, methyl salicylate, natural wintergreen, natural cool mint, natural wintermint, peppermint ocean, and/or crème de menthe. Examples of sweeteners include sucralose, xylitol, sodium saccharine, aspartame, and *stevia*. Furthermore, xylitol has been found to exhibit antimicrobial effects. Flavorant(s), sweetener(s), and colorant(s) may each be included in an amount in a range of about 0.1% to about 10% by weight, preferably from about 0.5% to about 8% by weight, and more preferably from about 1% to about 5% by weight.

A rheology modifying agent may also be included if desired. Fumed silica is a useful rheology modifying agent and has been found to thicken the composition for improved handling, as well as reducing the tendency of insoluble fluoride salts to settle during storage. Rheology modifying component(s) may be included in an amount in a range of about 0.1% to about 10% by weight, preferably in a range of about 0.5% to about 8% by weight, and more preferably in a range of about 1% to about 5% by weight.

Advantageously, the dental varnish compositions are sufficiently adhesive so as to allow the practitioner to brush, paint, or otherwise apply the composition onto a patient's teeth without having to worry about the composition running or dripping off. Exemplary adhesive compositions may have a relatively low viscosity (e.g., less than about 1000 centipoise). For example, the dental varnish compositions may have a viscosity of about 200 centipoise to about 800 centipoise, preferably about 300 centipoise to about 600 centipoise.

The dental varnish compositions can be formulated to temporarily adhere to tooth tissue (e.g., for a period of at least about 4 minutes, but not more than about 1 year, more typically about 5 minutes to about 90 days, more typically about 30 minutes to about 5 days). Over time, the varnish composition can spontaneously wear away as a natural result of the action of the tongue, saliva and/or other factors. The varnish composition may also be removed by applying mechanical action, for example, by brushing.

III. Exemplary Mixing Systems and Methods

Figure 1:
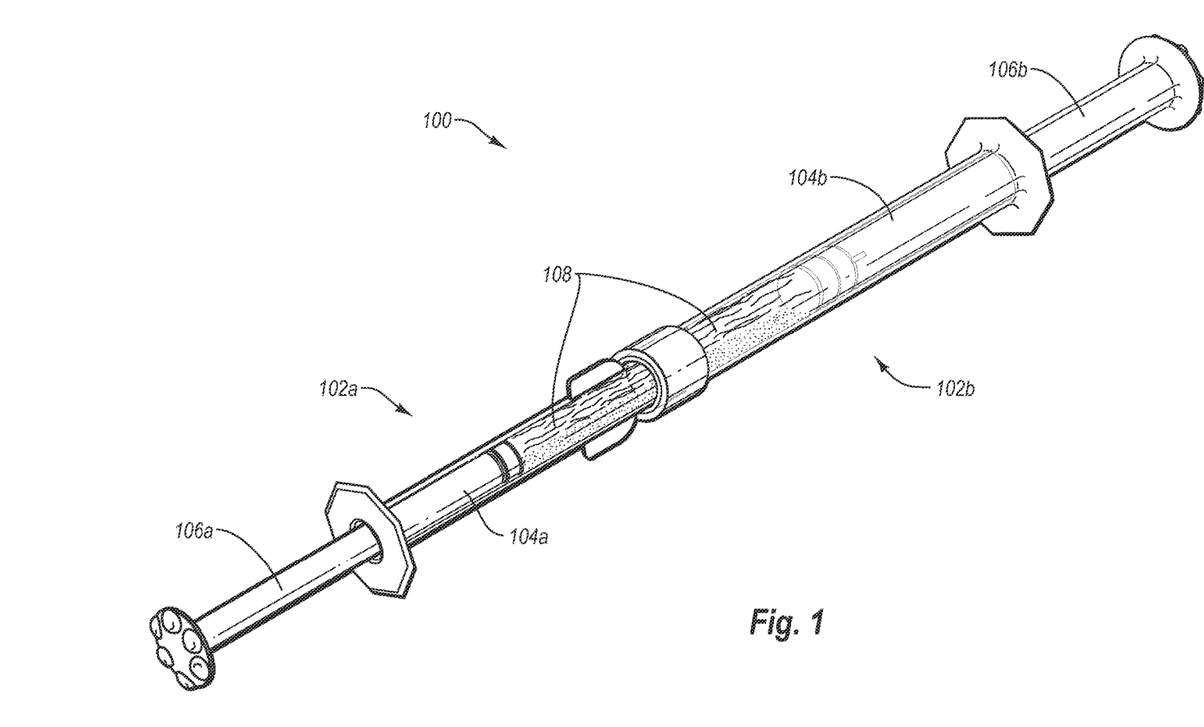
FIG. 1 is a perspective view of an exemplary two-syringe closed vessel mixing system that contains a multi-part fluoride varnish composition.

FIG. 1 illustrates a syringe-to-syringe mixing system 100 for mixing a dental varnish composition preparatory to applying it to a person's teeth. Mixing system 100 includes a first syringe 102*a* coupleable to a second syringe 102*b*. First syringe 102*a* includes a first barrel 104*a* and a first plunger 106*a* slidably disposed within first barrel 104*a*. First plunger 106*a* forms a seal against the inner wall of first barrel 104*a*, allowing plunger 106*a* to push the contents of barrel 104*a* out of the barrel. Second syringe 102*b* includes a second barrel 104*b* and a second plunger 106*b* disposed within second barrel 104*b*. First syringe 102*a* and second syringe 102*b* are illustrated as being coupled together so as to allow the dental varnish composition 108 to be cycled back and forth between the syringes so as to substantially suspend any solid particles (e.g., insoluble fluoride salts, calcium ion salts, and/or phosphate ions salts) phase within a generally hydrophobic liquid carrier phase of the composition.

Figure 2A:
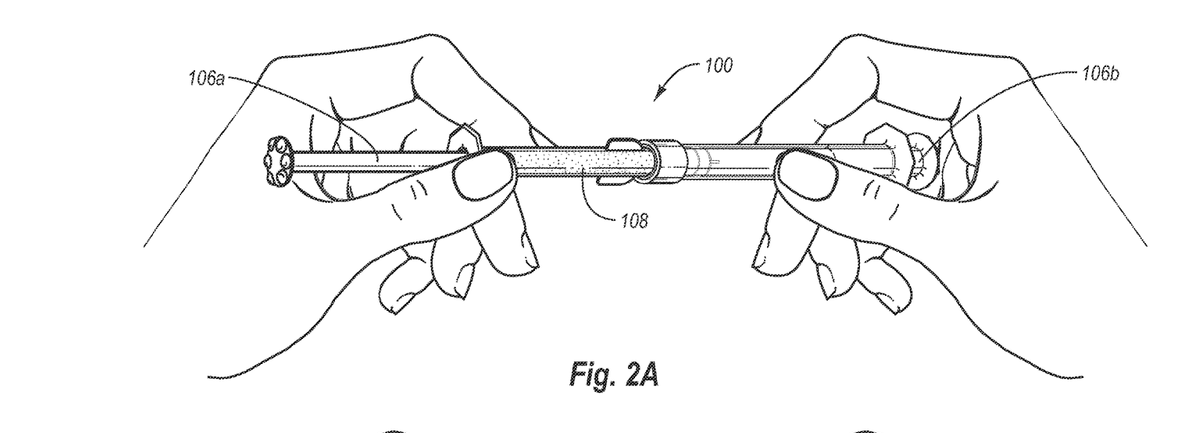
FIGS. 2A-2B depict the exemplary closed vessel mixing system of FIG. 1 being used to cycle the multi-part fluoride varnish composition back and forth.
Figure 2B:
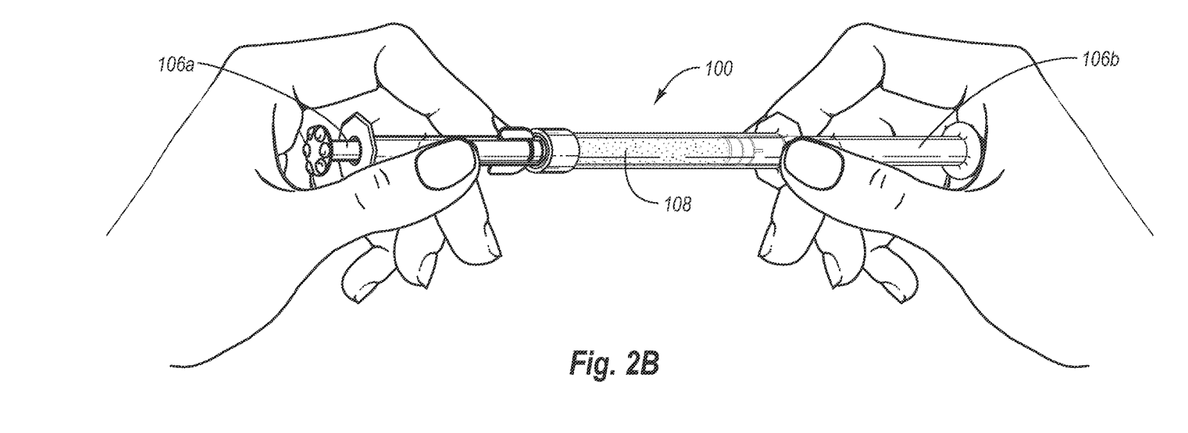

As illustrated in FIGS. 2A and 2B, a dental practitioner is able to apply turbulence to the multi-phase dental varnish composition 108 within first and second syringes of system 100 by manipulating plungers 106*a* and 106*b* so as to cycle the varnish composition 108 back and forth. In such a mixing system the dental varnish composition may be cycled back and forth as many times as desired so as to substantially suspend the solid particle phase within the liquid phase of the composition.

System 100 may advantageously be configured so as to contain a single use quantity of the multi-phase dental varnish composition 108. Such a system advantageously provides a single use system that can be provided to the dental practitioner as a uni-dose system which can be mixed and applied to the teeth of a single patient, after which the empty syringe-to-syringe mixing apparatus can be discarded.

Such a syringe-to-syringe configuration is effective in suspending insoluble particulate components of the composition within the carrier as particles (e.g., fluoride salts) may tend to settle out during storage. The inclusion of fumed silica within the composition may reduce or eliminate settling. In addition, the syringe-to-syringe configuration is effective in mixing together any other components of the varnish composition that may tend to form separate phases during prolonged storage. For example, compositions not including a solubilizing agent (e.g., polysorbate 80) to help prevent the resin from separating from other components of the carrier may tend to form separate phases during storage. If such is the case with any given varnish composition, the syringe-to-syringe configuration allows for quick and easy remixing of the composition prior to application to a patient's teeth.

Figure 3A:
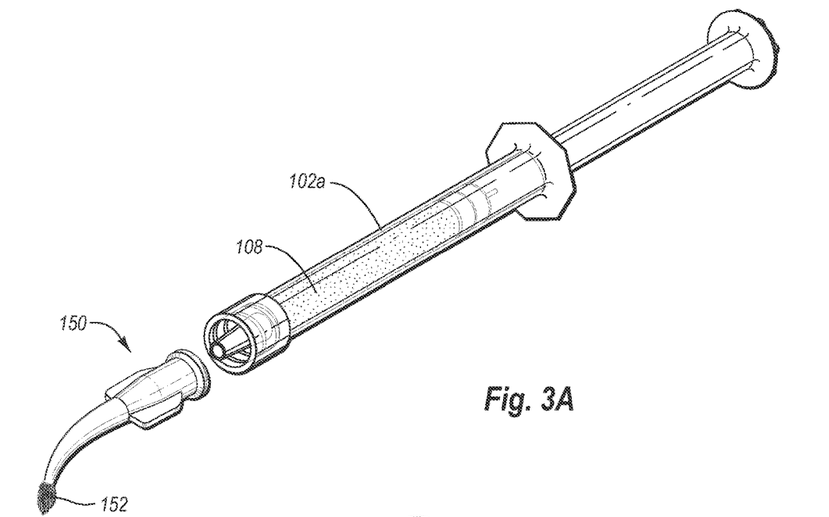
FIGS. 3A-3B illustrate a syringe (e.g., from the mixing system of FIG. 1) being coupled to a flocked applicator tip.
Figure 3B:
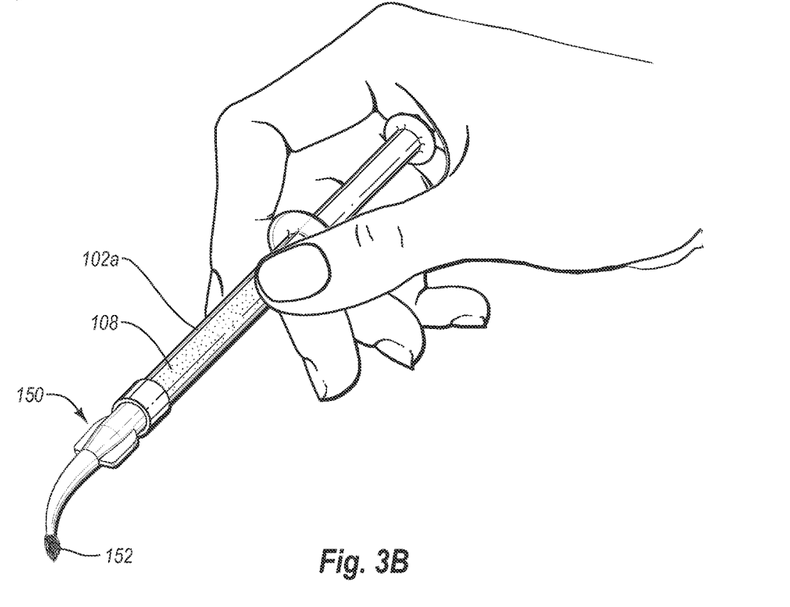

Once the solid particles (e.g., fluoride salt) has been suspended, the dental varnish composition may be applied to a person's teeth. According to one method, as seen in FIGS. 3A-3B, an applicator tip 150 may be coupled to syringe 102*a* containing the varnish composition 108 after the syringe has been separated from the remainder of the mixing system. Tip 150 may be coupled to first syringe 102*a* so as to allow a dental practitioner to dispense dental varnish composition 108 onto a person's teeth. As illustrated, applicator tip 150 may include a flocked tip 152 so as to allow the user to paint the composition 108 onto the teeth. Use of an applicator tip 150 including a flocked tip 152 are particularly useful, although other types of tips (e.g., a tip including a foam pad, a cotton swab, or other absorbent material) can be used.

Figure 4:
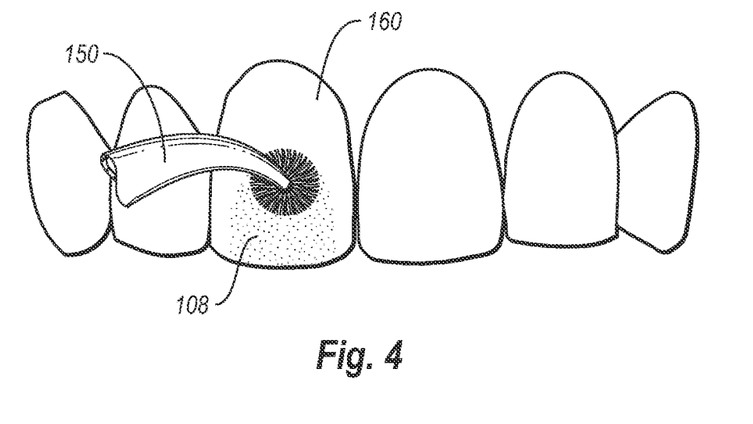
FIG. 4 illustrates the application of a fluoride varnish composition to a tooth using a flocked applicator tip.

FIG. 4 illustrates a dental practitioner using applicator tip 150 to apply varnish composition 108 to a person's tooth 160. Dental varnish composition 108 may be substantially colorless or, alternatively, it may provide a visual contrast against the surface of a person's teeth to allow a dental practitioner to easily determine where the composition has been applied. Suspension of the particulate phase (and/or remixing of other components) advantageously provides an even distribution of the active agent (e.g., fluoride salt), carrier, and other components to the teeth, providing a more consistent concentration of active agent and more consistent adhesion characteristics, resulting in overall better treatment across the full surface area of the tooth being treated. Although dispensing and application of the varnish composition is described using syringe-to syringe mixing device 100, it is understood that any apparatus or method of application may be used. Alternative devices that can be used to suspend and dispense the fluoride varnish composition are disclosed in U.S. patent application Ser. No. 11/348,055 filed Feb. 6, 2006 and entitled METHODS AND SYSTEMS FOR MIXING A MULTI-PART FLUORIDE VARNISH COMPOSITION, and U.S. patent application Ser. No. 12/258,746 filed Oct. 27, 2008 entitled MIXING DEVICE INCLUDING A PLUNGING MIXING MEMBER FOR USE WITH A SYRINGE, each of which is incorporated herein by reference.

The dental varnish composition can be formulated to remain adhered to a person's teeth for an extended period of time relative to typical in-office fluoride treatments, yet still be temporary. For example, the varnish may remain adhered for at least about 4 minutes, but no more than about 1 year, more preferably at least about 5 minutes but not more than about 90 days. In one embodiment, the varnish composition may remain adhered to a person's teeth for at least about 30 minutes, preferably at least about 2 hours, more preferably at least about one day, and most preferably at least about two days. Nevertheless, such compositions may wear away in about 5 days or less. Advantageously, the varnish composition can spontaneously wear away as a natural result of the action of the tongue, saliva and/or other factors within a temporary period, typically no more than about 5 days. Of course, the composition may be removed earlier than it would wear away naturally, for example, by aggressive brushing. A small fraction of the varnish composition may remain adhered to interproximal spaces between teeth (e.g., as long as 7-10 days) absent removal by aggressive brushing and/or flossing.

Extended adherence by the varnish composition to tooth tissue is advantageous as the tooth tissues can be exposed to the active agent (e.g., fluoride ions) for significantly longer times than is possible with in-office treatments or other treatments in which exposure to teeth is significantly less than what is provided by the disclosed varnish compositions. In particular, extended adherence to interproximal spaces between teeth may be particularly advantageous as these locations often harbor tooth decay.

IV. Examples

Following are examples of dental varnish compositions within the scope of the disclosure, most of which have been found to be stable over time so as resist formation of precipitates or other solids that can plug a syringe brush applicator tip, as well as a comparative example of a composition that is not stable over time but can result in plugging of a syringe brush applicator tip after storage for several months.

Examples 1-7

Examples 1-7 illustrate the beneficial effect of substituting at least a portion of Foral® AX acidic hydrogenated wood rosin with Foral® NC, the sodium neutralized form of acidic hydrogenated wood rosin, and then adding an acid to lower the pH. The composition of Example 1 includes Foral® AX acidic hydrogenated wood rosin as the sole resin component. This composition is very translucent and flowable when initially manufacture but over time (e.g., 3 months or more) can become less translucent (e.g., white) and gritty. In some cases, depending on the size or gauge of the syringe brush applicator tip, the composition of Example 1 can plug the applicator tip.

| Component (Mass %) | Example 1 | 2 | 3 | 4 | 5 | 6 | 7 |
|---|---|---|---|---|---|---|---|
| Foral ® AX | 60.9995 | | 28.27 | 54.6 | 51.6 | 49.51 | 25.25 |
| Foral ® NC | | 49.39 | 28.27 | 7 | 7.75 | 8.1 | 8.5 |
| Pexite FF | | | | 2.24 | 1.25 | 25.25 | |
| Pexalyn 295 | | | | | | | |
| Pentalyn FC | | | | | 1.25 | | |
| Enderes S | | 10 | | | | | |
| Stayelite Ester 10-A | | | | | | | |
| Hercolyn D | | 5 | 5 | | | | |
| Pentalyn H-A | | | | | | | |
| Ethyl Alcohol 100% | 23.9 | 19 | 25 | 25.28 | 25.28 | 25.28 | 25.29 |
| Hexadecane phosphate | 5 | 5 | 5 | 5 | 5 | 5 | 5 |
| Sodium Fluoride | 5 | 5 | 5 | 5 | 5 | 5 | 5 |
| Sucralose Powder | 0.5 | 0.5 | 0.5 | 0.5 | 0.5 | 0.4 | 0.4 |
| Saccharin | | | | | | 0.08 | 0.08 |
| Xylitol | 0.5005 | 0.01 | 0.01 | 0.01 | 0.02 | 0.01 | 0.01 |
| Stevia | | | | | | 0.01 | 0.01 |
| Citric Acid | | 3 | 0.35 | | | | |
| Phosphoric Acid | | | | | | 0.01 | 0.01 |
| Boric Acid | | | | 0.01 | | | 0.1 |
| Polysorbate 80 (Tween 80) | 0.1 | 0.1 | 0.1 | 0.1 | 0.01 | 0.01 | 0.11 |
| Peppermint Ocean | | 3 | 2.5 | 2.5 | 2.5 | | |
| Natural Wintermint | 0.65 | | | | | 0.65 | 0.65 |
| Natural Cool Mint | 2.7 | | | | | 2.7 | 2.7 |
| Methyl Salicylate | 0.65 | | | | | 0.65 | 0.65 |

The varnish compositions of Examples 2-7 remained more translucent and resisted formation of grittiness over time as compared to Example 1.

| Component (Mass %) | Example 8 | 9 | 10 | 11 | 12 | 13 | 14 |
|---|---|---|---|---|---|---|---|
| Foral ® AX | 25.25 | | | | 5.5 | 6.5 | |
| Foral ® NC | 8.5 | 8.5 | 8.5 | 16 | 18.5 | 18.5 | 21.94 |
| Pexite FF | 25.25 | 25.25 | | | | 14.23 | 23.8 |
| Pexalyn 295 | | | 23.25 | 20.14 | 15.1 | | |
| Pentalyn FC | | | 23.25 | 20.14 | 10.7 | 10.6 | 5.1 |
| Enderes S | 1.1 | 1.1 | 0.9 | | 5 | 7 | 6.5 |
| Stayelite Ester 10-A | | | | 1.6 | | | |
| Hercolyn D | | | | | 0.5 | 0.5 | 1 |
| Pentalyn H-A | | 2 | 2 | 2 | 4.5 | 2.5 | 1 |
| Ethyl Alcohol 100% | 25.17 | 23.84 | 25.17 | 26.17 | 26.15 | 25.92 | 25.05 |
| Hexadecane phosphate | 5 | 5 | 5 | 5 | 5 | 5 | 5 |
| Sodium Fluoride | 5 | 5 | 5 | 5 | 5 | 5 | 5 |
| Sucralose Powder | 0.4 | 0.4 | 0.4 | 0.5 | 0.5 | 0.5 | 0.4 |
| Saccharin | 0.08 | 0.08 | 0.08 | | | | |
| Xylitol | 0.01 | 0.01 | | 0.03 | 0.03 | 0.03 | 0.01 |
| Stevia | 0.01 | 0.01 | 0.02 | 0.01 | | | |
| Citric Acid | 0.1 | 0.2 | 0.3 | 0.3 | 0.4 | 0.5 | 1.5 |
| Phosphoric Acid | 0.01 | 0.01 | 0.01 | | 0.02 | | |
| Boric Acid | | | | 0.01 | | 0.02 | 0.5 |
| Polysorbate 80 (Tween 80) | 0.12 | 0.1 | 0.12 | 0.1 | 0.1 | 0.2 | 0.2 |
| Peppermint Ocean | | | | 3 | 3 | 3 | |
| Natural Wintermint | 0.65 | 0.65 | 0.65 | | | | 0.55 |
| Natural Cool Mint | 2.7 | 2.7 | 2.7 | | | | 1.9 |
| Methyl Salicylate | 0.65 | 0.65 | 0.65 | | | | 0.55 |

The varnish compositions of Examples 8-14 remained more translucent and resisted formation of grittiness over time as compared to Example 1.

| Component (Mass %) | Example 15 | 16 | 17 | 18 | 19 | 20 | 21 |
|---|---|---|---|---|---|---|---|
| Foral ® AX | 20 | 18 | 18 | | | | 6.75 |
| Foral ® NC | 29.09 | 30.99 | 33 | 36 | 38.5 | 38.5 | 45.5 |
| Pexite FF | | | | 10 | 7.5 | | |
| Pexalyn 295 | | 5.1 | | | | | |
| Pentalyn FC | 5.1 | | | 4.9 | 4.9 | 5.25 | |
| Enderes S | | 2.84 | 5.9 | 5.9 | 5.9 | 4.47 | 4.47 |
| Stayelite Ester 10-A | 2.84 | | | | | 8.5 | |
| Hercolyn D | 1.5 | 1 | | | 0.75 | 2 | 2 |
| Pentalyn H-A | 0.5 | 1 | 2 | 2 | 1.25 | | |
| Ethyl Alcohol 100% | 25.05 | 25.05 | 25.05 | 25.05 | 25.05 | 25.05 | 25.05 |
| Hexadecane phosphate | 5 | 5 | 5 | 5 | 5 | 5 | 5 |
| Sodium Fluoride | 5 | 5 | 5 | 5 | 5 | 5 | 5 |
| Sucralose Powder | 0.5 | 0.5 | 0.6 | 0.6 | 0.6 | 0.6 | 0.6 |
| Saccharin | | | | | | | |

-continued

| Component (Mass %) | Example | | | | | | |
|---|---|---|---|---|---|---|---|
| | 15 | 16 | 17 | 18 | 19 | 20 | 21 |
| Xylitol | 0.01 | 0.01 | 0.01 | 0.01 | 0.01 | 0.01 | 0.01 |
| Stevia | | | | | | | |
| Citric Acid | 2.2 | 2.3 | 2.3 | 2.4 | 2.4 | 2.4 | 2.6 |
| Phosphoric Acid | 0.01 | | 0.01 | 0.01 | 0.02 | | |
| Boric Acid | | 0.01 | 0.01 | 0.01 | | 0.01 | |
| Polysorbate 80 (Tween 80) | 0.2 | 0.2 | 0.2 | 0.2 | 0.2 | 0.2 | 0.1 |
| Peppermint Ocean | | | | | | | |
| Natural Wintermint | 0.55 | 0.55 | 0.6 | 0.6 | 0.6 | 0.6 | 0.6 |
| Natural Cool Mint | 1.9 | 1.9 | 1.82 | 1.82 | 1.82 | 1.82 | 1.82 |
| Methyl Salicylate | 0.55 | 0.55 | 0.5 | 0.5 | 0.5 | 0.5 | 0.5 |

The varnish compositions of Examples 15-21 remained more translucent and resisted formation of grittiness over time as compared to Example 1.

| Component (Mass %) | Example | | | | | | |
|---|---|---|---|---|---|---|---|
| | 22 | 23 | 24 | 25 | 26 | 27 | 28 |
| Foral ® AX | 5.75 | | | | | 1.36 | 1.36 |
| Foral ® NC | 46.92 | 50.5 | 57.43 | 60 | 61.5 | 50.25 | 47.5 |
| Pexite FF | | | | | | | 3.75 |
| Pexalyn 295 | | | | | | | |
| Pentalyn FC | | | | | | | |
| Enderes S | 4.47 | 8.43 | 1.5 | | | 10 | 10 |
| Stayelite Ester 10-A | | 2 | 2 | 2 | | | |
| Hercolyn D | 2 | 2 | | 1 | 1 | 1 | 1 |
| Pentalyn H-A | | | | 1 | 1 | 1 | 1 |
| Ethyl Alcohol 100% | 25.05 | 20.75 | 22.75 | 19.67 | 19.78 | 19.78 | 18.78 |
| Hexadecane phosphate | 5 | 5 | 5 | 5 | 5 | 5 | 5 |
| Sodium Fluoride | 5 | 5 | 5 | 5 | 5 | 5 | 5 |
| Sucralose Powder | 0.6 | 0.6 | 0.6 | 0.5 | 0.5 | 0.5 | 0.5 |
| Saccharin | | | | | | | |
| Xylitol | 0.01 | 0.01 | 0.01 | 0.01 | 0.01 | 0.01 | 0.01 |
| Stevia | | | | | | | |
| Citric Acid | 2.6 | 3 | 3 | 3.1 | 3.1 | 3 | 3 |
| Phosphoric Acid | | | | | | | |
| Boric Acid | | 0.01 | 0.01 | 0.02 | 0.01 | | |
| Polysorbate 80 (Tween 80) | 0.1 | 0.2 | 0.2 | 0.2 | 0.1 | 0.1 | 0.1 |
| Peppermint Ocean | 2.5 | 2.5 | 2.5 | 2.5 | 3 | 3 | 3 |
| Natural Wintermint | | | | | | | |
| Natural Cool Mint | | | | | | | |
| Methyl Salicylate | | | | | | | |

The varnish compositions of Examples 22-28 remained more translucent and resisted formation of grittiness over time as compared to Example 1.

The compositions made according to Examples 2-28 are very similar to the composition of Example 1 in that they all include similar amounts of wood rosin derivatives. However, Examples 2-28 all included some amount of Foral® NC, which, surprisingly and unexpectedly, yielded varnish compositions that were more stable, translucent and less gritty over time as compared to the varnish of Example 1. This was so even though Examples 2-28 were acidified using one or more acids in order to reduce the pH to the same of similar pH as Example 1. Thus, neutralizing highly acidic hydrogenating wood rosin using a base such as sodium carbonate and then re-acidifying the neutralized hydrogenating wood rosin resulted in a highly hydrogenated and acidic wood rosin that nevertheless remained more stable over time.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A stable dental varnish composition for application to a person's teeth, comprising:
   a stable liquid or gel carrier and an active agent dispersed within the carrier,
   the liquid or gel carrier comprising a solvent, a resin component, and an acidifying component,
   the resin component comprising an at least partially neutralized hydrogenated wood rosin with an initial pH of 6 or more before being combined with the acidifying component,
   the acidifying component comprising at least one organic or inorganic acid in an amount so that the pH of the liquid or gel carrier is below 5.

2. A stable dental varnish composition as in claim 1, wherein the at least partially neutralized hydrogenated wood rosin has a natural pH of about 3 or below before neutralization with a base.

3. A stable dental varnish composition as in claim 2, wherein the at least partially neutralized hydrogenated wood rosin has an initial pH in a range of about 6 to 7 as a result of neutralization with an alkali metal base and before being combined with the acidifying agent.

4. A stable dental varnish composition as in claim 1, wherein the at least partially neutralized hydrogenated wood rosin is a partial sodium resinate formed by treating an acidic hydrogenated wood rosin with sodium carbonate.

5. A stable varnish composition as in claim 1, wherein the acidifying component comprises an acid selected from the group consisting of citric acid, phosphoric acid, boric acid, malic acid, and mixtures thereof.

6. A stable dental varnish composition as in claim 1, wherein the acidifying component is included in an amount so that the pH of the liquid or gel carrier is about 4 or below.

7. A stable dental varnish composition as in claim 1, wherein the acidifying component is included in an amount so that the pH of the liquid or gel carrier is about 3.5 or below.

8. A stable dental varnish composition as in claim 1, wherein the acidifying component is included in an amount so that the pH of the liquid or gel carrier is about 3 or below.

9. A stable dental varnish composition as in claim 1, wherein the dental varnish composition is stable for at least about 3 months so as to remain translucent and not form solids that plug a 25 gauge or smaller syringe brush applicator tip.

10. A stable dental varnish composition as in claim 1, wherein the dental varnish composition is stable for at least about 6 months so as to remain translucent and not form solids that plug a 30 gauge or smaller syringe brush applicator tip.

11. A stable dental varnish composition as in claim 1, wherein the dental varnish composition is translucent.

12. A stable dental varnish composition as in claim 1, further comprising an organo phosphoric acid having at least one alkyl group for increasing adhesion of the varnish composition to a tooth surface.

13. A stable dental varnish composition as recited in claim 12, wherein the organo phosphoric acid comprises an alkyl phosphoric acid having at least one alkyl group with 3 to 30 carbon atoms.

14. A stable dental varnish composition as recited in claim 1, wherein the solvent comprises an organic solvent and wherein the dental varnish composition is substantially anhydrous.

15. A stable dental varnish composition as in claim 14, wherein the active agent comprises a fluoride ion source.

16. A stable dental varnish composition as recited in claim 15, wherein the active agent further comprises at least one of a calcium ion source or a phosphate ion source.

17. A method of treating a person's teeth, comprising:
applying a stable dental varnish composition as recited in claim 1 to one or more tooth surfaces; and
permitting the dental varnish composition to remain on the one or more tooth surfaces for a time sufficient to provide a desired treatment.

18. A stable fluoride varnish composition for application to a person's teeth, comprising:
a stable liquid or gel carrier and a fluoride ion source dispersed within the carrier,
the liquid or gel carrier comprising a resin component and an acidifying component,
the resin component comprising a partial sodium resinate of acidic hydrogenated wood rosin formed by treating acidic hydrogenated wood rosin with sodium carbonate to raise its pH to at least about 6 before being combined with the acidifying component,
the acidifying component comprising at least one organic or inorganic acid in an amount so that the pH of the liquid or gel carrier is below about 4,
wherein the fluoride varnish composition is stable for at least about 3 months so as to remain translucent and not form solids that plug a 25 gauge or smaller syringe brush applicator tip.

19. A method of providing fluoride treatment to a person's teeth, comprising:
applying a stable fluoride varnish composition as recited in claim 18 to one or more tooth surfaces; and
permitting the fluoride varnish composition to remain on the one or more tooth surfaces for a time sufficient to provide fluoride treatment.

20. A method of manufacturing a stable dental varnish composition as in claim 1, comprising:
preparing a stable liquid or gel carrier by mixing together the at least partially neutralized hydrogenated wood rosin, the solvent, and the acidifying agent to lower the pH of the carrier to below 5; and
adding the active agent before, during or after formation of the stable liquid or gel carrier.

21. A stable dental varnish composition for application to a person's teeth, comprising:
a stable liquid or gel carrier and an active agent dispersed within the carrier,
the liquid or gel carrier comprising a solvent, a resin component, and an acidifying component,
the resin component comprising an at least partially neutralized hydrogenated wood rosin with an initial pH of above 5 before being combined with the acidifying component,
the acidifying component comprising at least one organic or inorganic acid in an amount so that the pH of the liquid or gel carrier is below 5,
wherein the fluoride varnish composition is stable for at least about 3 months so as to remain translucent and not form solids that plug a 25 gauge or smaller syringe brush applicator tip.

* * * * *